US009173823B2

(12) United States Patent
Veillet et al.

(10) Patent No.: US 9,173,823 B2
(45) Date of Patent: Nov. 3, 2015

(54) PREPARATION FOR SUN PROTECTION

(75) Inventors: Stanislas Veillet, Savigny sur Orge (FR); René Lafont, Paris (FR); Waly Dioh, Bretigny sur Orge (FR)

(73) Assignees: INSTITUT BIOPHYTIS SAS, Romainville (FR); UNIVERSITE PIERRE ET MARIE CURIE, Paris (FR)

( * ) Notice: Subject to any disclaimer, the term of this patent is extended or adjusted under 35 U.S.C. 154(b) by 0 days.

(21) Appl. No.: 13/380,768

(22) PCT Filed: Jun. 25, 2010

(86) PCT No.: PCT/FR2010/051323
§ 371 (c)(1),
(2), (4) Date: Feb. 27, 2012

(87) PCT Pub. No.: WO2010/149942
PCT Pub. Date: Dec. 29, 2010

(65) Prior Publication Data
US 2012/0149776 A1 Jun. 14, 2012

(30) Foreign Application Priority Data
Jun. 25, 2009 (FR) .................................... 09 54354

(51) Int. Cl.
| A61K 9/00 | (2006.01) |
| A61K 8/362 | (2006.01) |
| A61K 8/37 | (2006.01) |
| A61K 8/97 | (2006.01) |
| A61K 36/185 | (2006.01) |
| A61Q 17/04 | (2006.01) |

(52) U.S. Cl.
CPC . *A61K 8/362* (2013.01); *A61K 8/37* (2013.01); *A61K 8/97* (2013.01); *A61K 36/185* (2013.01); *A61Q 17/04* (2013.01); *A61K 2800/92* (2013.01)

(58) Field of Classification Search
None
See application file for complete search history.

(56) References Cited

U.S. PATENT DOCUMENTS

| 5,032,382 A | 7/1991 | Grollier et al. | |
| 2003/0104090 A1* | 6/2003 | Levy et al. | 424/776 |

FOREIGN PATENT DOCUMENTS

EP 1484051 A2 12/2004

OTHER PUBLICATIONS

Hagiwara et al. (Food and Chemical Toxicology 41 (2003) 1157 1164, A thirteen-week oral toxicity study of annatto extract (norbixin), a natural food color extracted from the seed coat of annatto (*Bixa orellana* L.), in Sprague-Dawley rats).*

Vedavathy et al. (Natural food dye, Natural product Radiance vol. 2 (2) Mar.-Apr. 2003).*
Kroes et al. (WHO Food Additives Series: 52, Annatto Extracts, First draft prepared by Professor R. Kroes Institute for Risk Assessment Sciences, Utrecht University, Soest, Netherlands and Dr P. Verger National Institute for Agricultural Research, Safe Consortium on Food Safety, Brussels, Belgium, 2004).*
Codex Alimentarius Commission, Joint FAO/WHO Food Standards, 29 session, Geneva, Switzerland, Jul. 3-7, 2006.
21 C.F.R. § 73.30, Annatto extract, vol. 1, revised as of Apr. 1, 2002, pp. 346-347.
Anger et al., "Absence of carcinogenic and anticarcinogenic effects of annatto in the rat liver medium-term assay," Food and Chemical Toxicology, 2004, vol. 42, pp. 1687-1693.
Bautista et al., "Subacute toxicity assessment of annatto in rat," Food and Chemical Toxicology, 2004, vol. 42, pp. 625-629.
Biesalski et al., "UV light, beta-carotene and human skin—beneficial and potentially harmful effect," Archives of Biochemistry and Biophysics, May 1, 2001, vol. 389, No. 1, pp. 1-6.
Corol et al., "Diversity of Biological Functions of Carotenoids," Roumanian Biotechnological Letters, 2003, vol. 8, No. 1, pp. 1067-1074, Romania.
Fernandes et al., "Norbixin ingestion did not induce any detectable DNA breakage in liver and kidney but caused a considerable impairment in plasma glucose levels of rats and mice," Journal of Nature Biochemistry, 2002, vol. 13, pp. 411-420.
Garmyn et al., "Effect of β-carotene supplementation on human sunburn reaction," Exp. Dermatol, Apr. 1995, vol. 4, No. 2, pp. 104-111 (abstract).
Hagiwara et al., "A thirteen-week oral toxicity study of annatto extract (norbixin), a natural food color extracted from the seed coat of annatto (*Bixa orellana* L.), in Sprague-Dawley rats.," Food and Chemical Toxicology, 2003, vol. 41, pp. 1157-1164.
Heinrich et al., "Supplementation with β-carotene or a similar amount of mixed carotenoids protects Humans from UV-induced erythema," Journal of Nutrition, 2003, vol. 133, pp. 98-101.
Júnior et al., "Antigenotoxic and antimutagenic potential of an annatto pigment (norbixin) against oxidative stress," Genetics and Molecular Research, 2005, vol. 4, No. 1, pp. 94-99.
Kiokias et al., "Dietary supplementation with a natural carotenoid mixture decreases oxidative stress," European Journal of Clinical Nutrition, 2003, vol. 57, pp. 1135-1140.
Kovary et al., "Biochemical behaviour of norbixin during in vitro DNA damage induced by reactive oxygen species," British Journal of Nutrition, 2001, vol. 85, pp. 431-440.
Levy et al., "Bixin and norbixin in human plasma: determination and study of the absorption of a single dose of Annatto food color," Analyst, Sep. 1997, vol. 122, pp. 977-980.
Mercadante et al., "Isolation and structure elucidation of minor carotenoids from annatto (*Bixa orellana* L.) seeds," Phytochemistry, 1997, vol. 46, No. 8, pp. 1379-1383.
Richelle et al., "Skin bioavailability of dietary vitamin E, carotenoids, polyphenols, vitamin C, zinc and selenium," British Journal of Nutrition, 2006, vol. 96, pp. 227-238.
Russell et al., "The effect of annatto on insulin binding properties in the dog," Phytotherapy Research, 2005, vol. 19, pp. 433-436.
Sies et al., "Vitamins E and C, β carotene and other carotenoids as antioxydants," Am. J. Clin. Nutr., 1995, vol. 62 supplement, pp. 1315S-1321S.
Sies et al., "Carotenoids and UV protection," Photochem. Photobiol. Sci., 2004, vol. 3, pp. 749-752.

(Continued)

*Primary Examiner* — Snigdha Maewall
(74) *Attorney, Agent, or Firm* — Im IP Law PLLC; C. Andrew Im

(57) ABSTRACT

The invention relates to the use of norbixin and an urucum extract enriched in bixin and/or norbixin as a food. The invention also provides a food preparation comprising norbixin, bixin or an extract comprising at least bixin or norbixin, the preparation being intended to be administered orally, for the protection of mammalian skin against UV-radiation.

19 Claims, 1 Drawing Sheet

(56) References Cited

OTHER PUBLICATIONS

Silva et al., "Antioxidant action of bixin against cisplatin-induced chromosome aberrations and lipid peroxidation in rats," Pharmacol. Res. 2001, vol. 43, pp. 561-566.
Stahl et al., "Increased dermal carotenoid levels assessed by noninvasive reflection spectrophotometry correlate with serum levels in women ingesting betatene," J. Nutr., 1998, vol. 128, pp. 903-907.
Stahl et al., "Carotenoids and carotenoids plus vitamin E protect against ultraviolet light-induced erythema in humans," Am. J. Clin. Nutr. 2000, vol. 71, pp. 795-798.
Stahl et al., "Dietary tomato paste protects against ultraviolet light-induced erythema in humans," J. Nutr., 2001, vol. 131, pp. 1449-1451.
Stahl et al., "Lycopene-rich products and dietary photoprotection," Photochem. Photobiol. Sci., 2006, vol. 5, pp. 238-242.
Stahl et al., "Carotenoids and flavonoids contribute to nutritional protection against skin damage from sunlight," Mol. Biotechnol., 2007, vol. 37, pp. 26-30.
Thresiamma et al., "Protective effect of curcumin, ellagic acid and bixin on radiation induced genotoxicity," J. Exp. Clin. Cancer Res., 1998, vol. 4, pp. 431-443.
Paula R. Trumbo, "Are there adverse effects of lycopene exposure?," J. Nutr., 2005, vol. 135, pp. 2060S-2061S.
Young et al., "Antioxidant and prooxidant properties of carotenoids," Arch. Biochem. Biophys., 2001, vol. 385, pp. 20-27.
Sachan et al., "*Bixa orellana* L.—A dye yielding plant having medicinal properties," Medicinal & Aromatic Plants Abstracts, Scientific Publishers, New Delhi, India, vol. 25, No. 2, Apr. 1, 2003.
Evans,W.C., "Annatto: a natural choice," Biologist, Institute of Biology, London, Great Britain, vol. 47, No. 4, Sep. 1, 2000, pp. 181-184.
Srivastava et al., "Chemistry, Pharmacology and uses of *Bixa orellana*—A Review," Journal of Medicinal and Aromatic Plant Sciences,India, vol. 21, No. 21, Dec. 1, 1999, pp. 1145-1154.
Agner et al., "DNA damage and aberrant crypt foci as putative biomarkers to evaluate the chemopreventive effect of annatto (*Bixa orellana* L.) in rat colon carcinogenesis," Mutation Research, Genetic Toxicology and Environmental Mutagenesis, Elsevier, Amsterdam, Netherlands, vol. 582, No. 1-2, Apr. 1, 2005, pp. 146-154.
Jondiko et al., "Terpenoids and an apocarotenoid from seeds of *Bixa orellana*," Phytochemistry, Pergamon Press, Great Britain, vol. 28, No. 11, Jan. 1, 1989, pp. 3159-3162.
EFSA, "Opinion of the Scientific Panel on Food Additives, Flavourings, Processing Aids and Materials in Contacts with Food (AFC) on a request from the Commission related to Coumarin," The EFSA Journal, 2004, 104, pp. 1-36.
Nigg et al., "Phototoxic Coumarins in Limes," Fd Chem. Toxic., vol. 31, No. 5, pp. 331-335, 1983, Pergamon Press Ltd., Great Britain.
Halliwell et al., "Oxygen-derived Species: Their Relation to Human Disease and Environmental Stress," Environmental Health Perspectives, vol. 102, Suppl. 10, pp. 5-12, Dec. 1994.
Jaiswal et al., "Inflammatory Cytokines Induce DNA damage and Inhibit DNA repair in Cholangiocarcinoma Cells by a Nitric Oxide-dependent Merchanism," Cancer Research 60, pp. 184-190, Jan. 1, 2000.
Bau et al., "Nitric oxide is involved in arsenite inhibition of pyrimidine dimer excision," Carcinogenesis, vol. 22, No. 5, pp. 709-716, 2001.
Sakurai et al., "Detection of reactive oxygen species in the skin of live mice and rats exposed to UVA light: a research review on chemiluminescence and trials for UVA protection," Photochem. Photobiol. Sci., 4, pp. 715-720, 2005.
Pattison et al., "Actions of ultraviolet light on cellular structures," Cancer: Cell Structures, Carcinogens and Genomic Instability, edited by Leon P. Bignold, pp. 131-157, 2006, Brikhauser Verlag, Switzerland.
Walter et al., "Carotenoids and their cleavage products: Biosynthesis and functions," Nat. Prod. Rep. 28, pp. 663-692, 2011.
Liaaen-Jensen et al., "Charged Carotenoid Species," Studies in Natural Products Chemistry, Vo. 30, pp. 515-557, Atta-ur-Rahman (Ed.), Elsevier B.V, 2005.
Barcelos et al., "Bixin and Norbixin Protect Against DNA-Damage and Alterations of Redox Status Induced by Methylmercury Exposure in Vivo," Environmental and Molecular Mutagenesis, Aug. 2012, pp. 535-541, vol. 53, No. 7.
Koeneman et al., "Toxicity and celluar responses of intestinal cells exposed to titanium dioxide," Cell Biol Toxicol, 2010, 26: 225-238.
Krause et al., "Sunscreens: are they beneficial for health? An overview of endocrine disrupting properties of UV-filters," International Journal of Andrology, 2012, 35: 424-436.
Rhodes, "Topical and Systemic Approaches for Protection against Solar Radiation-Induced Skin Damage," Clinics in Dermatology, 1998, 16:75-82.
Schlumpf et al., "In Vitro and in Vivo Estrogenicity of UV Screens," Environmental Health Perspectives, Mar. 2001, pp. 239-244, vol. 109, No. 3.
Schlumpf et al., "Estrogenic activity and estrogen receptor β binding of the UV filter 3-benzylidene camphor Comparison with 4-methylvenzylidene camphor," Toxicology , 2004, 199: 109-120.

\* cited by examiner

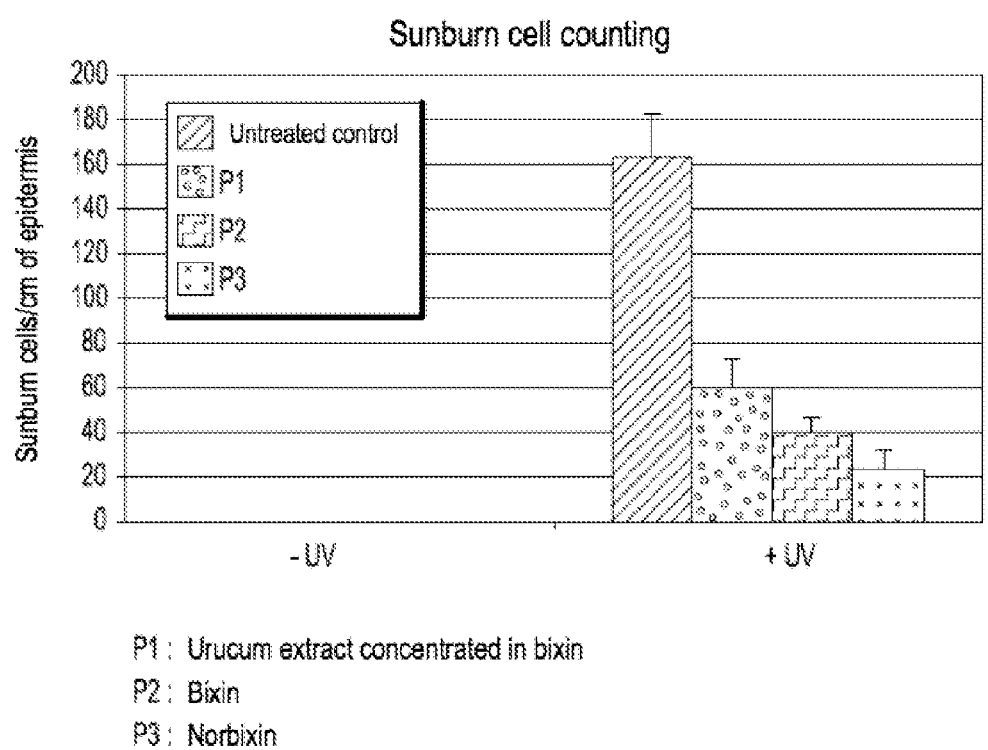

PREPARATION FOR SUN PROTECTION

RELATED APPLICATIONS

This application is a §371 application from PCT/FR2010/051323 filed Jun. 25, 2010, which claims priority from French Patent Application No. 09 54354 filed Jun. 25, 2009, each of which is herein incorporated by reference in its entirety.

TECHNICAL FIELD OF INVENTION

The invention relates to a preparation for cosmetic use to protect the skin against the harmful effects of solar ultraviolet radiation.

BACKGROUND OF THE INVENTION

It is known that solar radiation can be harmful to humans. Indeed, most solar energy is emitted as UV rays, which penetrate deeply into the epidermis. The skin protects itself from solar radiation, by synthesizing melanin, a pigment capable of absorbing UV rays and limiting their deep penetration into the dermis. However, the rate of melanin synthesis varies from one individual to another, and filtration is not sufficient to efficiently protect against the sun's photo damage. In particular, UV-B wavelengths (280-320 nm) cause sunburn on sensitive skin, or when skin is frequently exposed to sunlight. Similarly, UVA wavelengths (320-400 nm) are known to induce skin tanning, to accelerate skin aging and to be involved in the development of many skin cancers.

Many studies have been conducted to develop preparations, usually topical, to protect the skin when frequently exposed to sun. These preparations often include carotenoids, known to be used by plants to protect themselves from sun damage. Carotenoids are orange and yellow pigments and are frequently found in many other living organisms. They belong to the chemical family of isoprenoids and are liposoluble. They are synthesized by algae, green plants and many fungi and bacteria (including cyanobacteria). Animals are not able to produce carotenoids and consequently take them up from their food.

Carotenoids are known for their photoprotective activity, related to their absorption of light rays (screen barrier function) and also to their antioxidant properties, which enable them to effectively neutralize peroxyl radicals and singlet oxygen (Sies and Stahl, 1995, 2004). They can be used externally but also internally, because some of the carotenoids ingested by animals accumulate in the skin. Supplementation with β-carotene and lycopene, alone or mixed with other carotenoids, shows a systemic photoprotection, as measured by a decrease in UV-induced erythema.

A randomized cross-over clinical study showed that a mixture of carotenoids reduces oxidative stress. This study describes the effect of carotenoids in 32 individuals who were non-smokers and in good health who daily received for a period of 3 weeks and in cross-over, separated by a washout of 12 weeks 4 capsules containing, either 1 g of fish oil, or 1 g of fish oil supplemented with a mixture of carotenoids (7.6 mg of total carotenoids including 2.9 mg bixin per capsule). It was observed that the carotenoid mixture reduces the oxidative stress induced by fish oil (rich in the polyunsaturated fatty acids 20:5 and 20:6) consumption. This is illustrated by an increased stability of the LDL measured in an ex-vivo oxidation assay and by the reduced concentration of a DNA-damage marker (8-hydroxy-2'-deoxyguanosine) in urine (Kiokias and Gordon, 2003). Another study, performed in mice, showed that an oral administration of various carotenoids, including bixin (200 mg=80 micromoles per kilogram of body weight) before γ-irradiation (1.5-3.0 Gy) reduced the occurrence of chromosomal damage, assessed by the micronucleus test (Thresiamma et al., 1998). Bixin is also able to reduce the side-effects of chemotherapy when orally administered prior to its application (Silva et al., 2001).

The antioxidant activity of norbixin on plasmid DNA was studied by inducing breaks by free-radical hydrogen peroxide $H_2O_2$ in the presence of $Sn^{2+}$ or $Fe^{2+}$ ions in the Fenton reaction: low concentrations of norbixin (10 µM) protect plasmid DNA in the presence of 10 µM of $H_2O_2$ (Kovary et al., 2001). In addition, norbixin increases by a factor of 10 the survival of bacteria (*E. coli*) when subjected to UV-radiation in the presence of hydrogen peroxide $H_2O_2$ or superoxide anion $O_2.-$. The UV-C induced SOS system is reduced by 2.3 times in the presence of norbixin (Júnior et al., 2005). Finally, norbixin has a antimutagenic activity, and reduces by 87% the mutagenic effect of $H_2O_2$ on *Salmonella typhimurium* (Kovary et al., 2001).

More generally, it has been shown in cell-free systems that carotenoids can scavenge superoxide anions generated by the xanthine/xanthine oxidase system. The scavenging ability depends on the carotenoid and decreases in the order of canthaxanthin>bixin>lutein>β-carotene (Corol et al., 2003). For its antioxidant effects, bixin has been proposed to be included in foods (Levy and Levy, 2003).

Based on their properties, liposoluble carotenoids have been included in preparations to be applied to the skin before and during sun exposure in order to protect it from sun damage. Moreover, their pigmenting properties can allow the coloration of the epidermal cells layer in orange, thus accentuating the impression of tanning. A photostable screening cosmetic preparation has been developed to protect human skin against UV-radiation, including a small amount (0.0025 to 0.009% in weight) of bixin in an oily extract mixture (Grollier et al., 1991).

However, carotenoids may also be ingested and play their antioxidant role in the dermal and epidermal cells. The ingested compounds are indeed found in plasma and in various tissues, including skin (Richelle et al., 2006). The human skin contains an average of 0.2 to 0.6 ng/g of total carotenoids, with wide variations between individuals and between areas of the body within the same individual (Stahl and Sies, 2007). Ingestion of food supplemented with carotenoids increases its content in the dermis (Stahl et al., 1998). To be effective, food supplemented in carotenoids must be used for an extended period: longer than 10 weeks (Stahl et al., 2000).

Such an approach has shown its efficacy in several cases: a mixture of 30 to 90 mg/day for 24 weeks of β- and α-carotene (Lee et al., 1999), a tomato extract providing 16 mg/day of lycopene for 12 weeks (Stahl et al., 2001, 2006), an algal extract (*Dunaniella salina*) providing 24 mg/day of β-carotene, or a mixture (1:1:1) of β-carotene, lutein and lycopene for 12 weeks (Heinrich et al., 2003). The protective effects appear only gradually, and a single dose administration of 120 mg or a daily dose of 90 mg of β-carotene over 23 days is ineffective (Garmyn et al., 1995). However, Kläui et al. (1973) who proposed ingestion of mixtures of carotenoids including possibly bixin for skin protection against UV rays indicate that a treatment starting from 10 to 20 days before exposure to sunlight is sufficient.

Carotenoids are generally considered as low or non-toxic molecules (Agner et al., 2004), even at chronic doses of 3 g/kg in animals (Trumbo, 2005).

OBJECT AND SUMMARY OF THE INVENTION

Urucum (*Bixa orellana*) belongs to the family of the Bixaceae. This plant comes in the form of a tree of 5 to 10 meters in height, bearing at the end of its branches pod-shaped fruits containing seeds surrounded by a red-orange colored layer. Urucum is used to produce the food colorant annatto (=E160b), which is a mixture of carotenoids mainly composed of bixin ($C_{25}H_{30}O_4$), plus a small proportion of norbixin ($C_{24}H_{28}O_4$) and several related minor compounds (Mercadante et al., 1997). Norbixin is a water-soluble derivative formed by alkaline hydrolysis of bixin. Various methods of extracting the pigment from urucum seeds pericarp have been described. These extracts are devoid of toxicity (Hagiwara et al., 2003; Bautista et al., 2004). The conclusions of the JECFA (Joint WHO/FAO Executive Committee on Food and Additives) held on 20-29 Jun. 2006 recommended a daily acceptable dose of 12 mg/kg of bixin in an extract standardized at 92% bixin and 0.6 mg of norbixin/kg for an extract standardized at 91% of norbixin. E160b is used by the food industry for coloring oils and fats (butter, oil, margarine), some cheeses, rice, etc.

The chemical formulae of bixin and norbixin are described below.

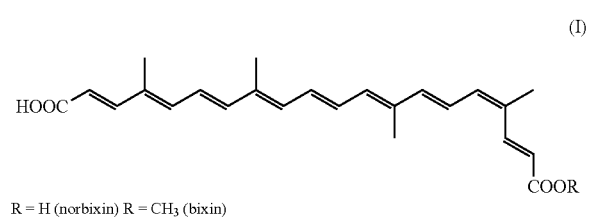

R = H (norbixin) R = CH₃ (bixin)

(I)

The inventors have discovered that human skin explants cultured for one week in the presence of bixin, norbixin or urucum extract (containing both molecules) acquire a high protection to UVB irradiation equivalent to about 2 MED. This protection results in a reduction of the sunburn cells (SBC) number observed 24 hours after irradiation (FIG. 1).

The inventors have observed that the decrease in SBC number is higher in the presence of norbixin (−84.4%) than with bixin (−74.4%) or urucum extract (−63.9%). This norbixin effect is observed for a concentration of 15.5 ng·mL$^{-1}$ (≈4.10$^{-8}$M).

Moreover, another study showed a dose-dependent effect on the protective activity of the urucum-enriched bixin extract at 166, 330 and 660 ng·mL$^{-1}$. With regard to alterations induced by UV-irradiation, this study shows reductions of 15% at 166 ng·mL$^{-1}$, 42% at 330 ng·mL$^{-1}$ and 63% at 660 ng·mL$^{-1}$.

It is known that ingested bixin is converted into norbixin, which is the main compound found in plasma after bixin ingestion. Following ingestion of an oily annatto solution containing 16 mg bixin, plasma concentrations higher than 25 ng·mL$^{-1}$ of norbixin were observed for more than 6 hours, whereas bixin only reached 10 ng·mL$^{-1}$, for less than 4 hours (Levy et al., 1997).

The invention therefore relates to an oral use of one molecule of formula (I) with R=CH₃ to prevent damage which may be caused by exposure to ultraviolet radiation on the skin of mammals.

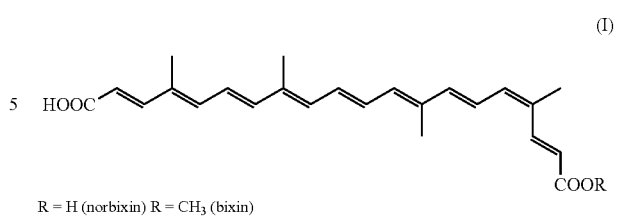

R = H (norbixin) R = CH₃ (bixin)

(I)

BRIEF DESCRIPTION OF THE DRAWINGS

FIG. 1: Effects of an urucum extract enriched in bixin, of bixin and norbixin on "sunburn cell" number following skin irradiation with the UV-B.

DETAILED DESCRIPTION OF THE EMBODIMENTS

In one embodiment of the invention, the first compound is mixed with a second molecule of formula (I) with R=H.

In one embodiment of the invention, the first molecule is ingested at a daily dose between 5 mg and 100 mg, preferably at a daily dose of 35 mg. In one example, the daily dose can be between 30 and 40 mg for a person weighing 70 kg.

In another embodiment of the invention, the second molecule is ingested at a daily dose between 5 mg and 100 mg, preferably at a daily dose of 35 mg. The invention also relates to a preparation to be administered orally, for the protection of mammalian skin against UV-radiation, characterized in that it comprises, in an acceptable carrier to be swallowed, one molecule formula (I) with R=CH₃ at a dose of at least 0.01% by weight of the first molecule to a maximum dose of 92% by weight of that first molecule.

In examples, the dose may be 0.001%, 0.01%, 0.1%, 1%, 2%, 5%, 7%, 10%, 15%, 20%, 25%, 30%, 35%, 40%, 45%, 50%, 55%, 60%, 65%, 70%, 75%, 80%, 85%, or 90%.

In one embodiment of the invention, the preparation also contains a second molecule of formula (I) with R=H.

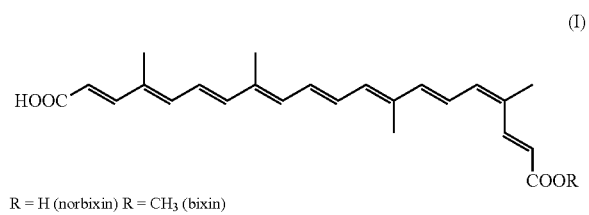

R = H (norbixin) R = CH₃ (bixin)

(I)

In one embodiment of the invention, the preparation comprises a minimal dose of 0.001% by weight of the second molecule to a maximum dose of 92% by weight of that second molecule. In examples, the dose may be 0.001%, 0.01%, 0.1%, 1%, 2%, 5%, 7%, 10%, 15%, 20%, 25%, 30%, 35%, 40%, 45%, 50%, 55%, 60%, 65%, 70%, 75%, 80%, 85%, or 90%.

In one embodiment of the invention, the first molecule is given as an urucum enriched extract in the first molecule of formula (I) with R=CH₃. In one embodiment of the invention, the extract contains urucum between 2% and 92% by weight of the first molecule, preferably at least 6% by weight of the first molecule.

In one embodiment of the invention, the second molecule is provided as an urucum extract enriched in the second molecule of formula (I) with R=H.

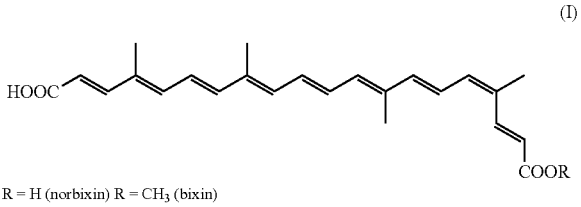

R = H (norbixin) R = CH₃ (bixin)

In one embodiment of the invention, the extract contains between 2% and 92% by weight of the second molecule, preferably at least 6% by weight of the second molecule.

In one embodiment of the invention, the preparation is prepared as a drug or dietary supplement or food. The invention also relates to an urucum extract, characterized in that it is enriched with a first molecule of formula (I) with R=CH₃, with the extract containing between 2% and 92% in weight, and preferably at least 6% in weight of the first molecule.

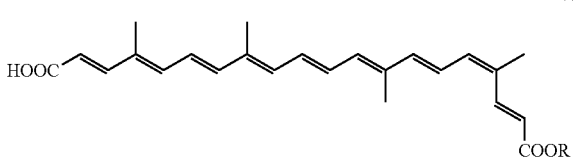

R = H (norbixin) R = CH₃ (bixin)

In one embodiment of the invention, the extract is also enriched with a second molecule of formula (I) with R=H, with the extract containing between 2% and 92% in weight, and preferably at least 6% by weight the second molecule.

Finally, the invention relates to the extract described above to formulate the preparation described above.

The first molecule of formula (I) with R=H is called norbixin.

The second molecule of formula (I) with R=CH₃ is called bixin.

The amount of bixin or norbixin recommended per day is 35 mg (in 2 doses) for a protective effect against solar radiation. This dosage is recommended for a person weighing about 70 kg.

The lower percentage in weight of norbixin or bixin is determined by a minimum concentration of norbixin or bixin. The minimum concentration of bixin or norbixin is a concentration below which norbixin or bixin according to the invention has no biological effect or photoprotective effect.

Norbixin or bixin can be obtained by extraction from plants containing norbixin or bixin. The plant preferably used to extract norbixin or bixin is urucum.

By 'preparation', one means a food-stuff, beverage, a dairy product or other. The preparation may be a medicinal preparation used such as pills, capsules or tablets which contain a precise dose of the first molecule of formula (I) with R=H. Medicinal preparation means a preparation having preventative properties towards solar radiation on the skin of a mammal.

The preparation contains between 2% and 92% by weight of the first molecule or second molecule, and preferably at least 6% by weight of the first molecule or second molecule.

By 'enriched' one means that the extract contains the first or second molecule in quantity as obtained by the extract preparation method described below. The composition of such capsules containing the enriched extract is made so that a capsule contains 17.5 mg of bixin or norbixin. Cassava starch is used to complete the formula. This can be for example 250 mg of an urucum extract containing 7% bixin and 263 mg of cassava starch.

The percentage by weight of norbixin or bixin in the urucum extract is determined by a threshold concentration below which no effects (positive or negative) are observed. The percentage by weight of norbixin or bixin in the extract is also determined by the highest concentration beyond which adverse effects to human health or to the organism ingesting the extract may appear (e.g. inhibition of the photoprotective effect, toxic effect).

As previously mentioned, the preparation may include for example a food such as a beverage, a dairy product or other. The preparation may be a medicinal preparation used such as pills, capsules or tablets which contain a precise dose of norbixin or bixin enriched-extract. Medicinal preparation means a preparation having preventative properties towards solar radiation on mammalian skin.

Norbixin-, bixin- or urucum-enriched extract of the invention may be ingested as a capsule, tablet or pill or can be mixed with a food product such as cheese, yoghurt or milk.

"Dietary Supplement" has the meaning given by the European Directive 2002/46/CE, i.e. any food whose purpose is to supplement the normal diet and is a concentrated source of nutrients or any other substances with a nutritional or physiological effect alone or in combination, marketed in dose form, namely, under the forms such as capsules, pastilles, tablets, pills and other similar forms as well as sachets of powder, ampoules of liquids, vials equipped with a dropper and other similar forms of liquids and powders designed to be taken in measured small unit quantities.

"Food" has the meaning given in section 2 of the European regulation 178/2002 of the European Parliament. The term "food" means any substance or product, whether processed, partially processed or unprocessed, intended to be ingested or reasonably expected to be ingested by humans. This includes drink, chewing gum and any substance including water, intentionally incorporated into the food during its manufacture, preparation or treatment. It includes water after the point of compliance referred to in Article 6 of Directive 98/83/EC without prejudice to the requirements of Directives 80/778/EEC and 98/83/EC.

The term "food" does not cover:
animal feed;
live animals unless they are prepared for human consumption;
plants prior to harvesting;
drugs within the meaning of Directives 65/65/EEC (21) and 92/73/EEC (22);
cosmetics within the meaning of Council Directive 76/768/EEC (23);
tobacco and tobacco products within the meaning of Council Directive 89/622/EEC (24);
narcotics and psychotropic substances under the Single Convention on Narcotic Drugs, UN 1961 and UN Convention on Psychotropic Substances of 1971;
residues and contaminants "Drug" has the meaning given by the European Directive 65/65/EEC which is any substance or compound presented as having properties for treating or preventing disease in human or animal and/or any substance or composition that may be administered to man or animals to establish a medical diagnosis or to restoring, correcting or modifying organic functions in humans or animals 1. Example of a Process for Preparing an Urucum Extract Enriched in Bixin.

400 liters of absolute ethanol are added to 200 kg of urucum seeds. A first extraction is performed by stirring for 16 hours. Separation by centrifugation is performed and 400 liters of a first liquid extract A is obtained. Residues are re-extracted with 400 liters of absolute ethanol. Both extracts (800 liters) are mixed and the volume reduced to 80 liters; 10 kg of cassava starch are added and the whole mix is spray-dried to obtain 30 kg of dry matter.

2. Example of a Process for Preparing an Urucum Extract Enriched in Norbixin

The preparation of the norbixin enriched extract is made by a saponification of the bixin enriched extract by stirring the latter in an aqueous solution of NaOH (bixin:NaOH 1:3 mol/mol) for several hours at 37° C. Aliquots of the saponification reaction can be analyzed by HPLC up to a bixin conversion to norbixin close to 100%. Drying is made by evaporation of water at 50° C. and crystallized norbixin is stored at −20° C. (Kovary et al., 2001)

3. Experimental Study of the Effect of a Bixin-Enriched Urucum Extract, of Bixin and of Norbixin (FIG. 1).

Following treatment and UV-B irradiation of human skin explants, a Masson trichrome staining allows the visualization and counting of SBC.

3.1 Tested Products:
P1: urucum organic extract titrated at 6% bixin (330 ng·mL-1)
P2: pure bixin (15.5 ng·mL-1)
P3: pure norbixin (15.5 ng·mL-1)

3.2 Human Skin Explant Preparation 27 explants (3 per condition) with a diameter of 10 mm were prepared from an abdominoplasty. The explants were cultured at 37° C. in a humid atmosphere containing 5% $CO_2$. These explants were divided into nine (9) batches as follows:

| Batch | Number of human skin explants | Treatment | UV | Skin explants collection |
|---|---|---|---|---|
| Control day 0 | 3 | No | − | day 0 |
| Control | 3 | No | − | day 8 |
| Urucum extract | 3 | Urucum | − | day 8 |
| Bixin | 3 | Bixin | − | day 8 |
| Norbixin | 3 | Norbixin | − | day 8 |
| UV Control | 3 | No | + | day 8 |
| Urucum extract UV | 3 | Urucum | + | day 8 |
| Bixin UV | 3 | Bixin | + | day 8 |
| Norbixin UV | 3 | Norbixin | + | day 8 |

3.3 Treatment

Urucum extract was dissolved in DMSO. The three products were added to the medium on the first day (D0), in order to achieve the desired final concentrations. The final amount of DMSO in the medium still remained below 1%. The explants of the control batch received no treatment.

3.4 UV-Irradiation

On day 7, the explants were exposed to UVB at a dose of 0.30 J/cm$^2$ and UVA at a dose of 9 J/cm$^2$. Non-irradiated batches were placed in the dark during the whole irradiation time. Immediately after irradiation, the explants were put back into culture medium.

3.5 Sampling

At day 0, the three explants from the control group were removed and cut in half. One part was fixed in the widely used Bouin's fixative to observe the general morphology. The other was frozen and stored at −80° C.

At day 8, i.e. 24 hours after irradiation, the three explants from each batch were taken and processed in the same way.

3.6 Histology

After 48 hours of fixation in Bouin's fixative, samples were dried and impregnated in paraffin using a Leica 1020 automated dehydration controller.

Microscopic observations were made by optical microscopy using a Leica DMLB model, with the ×40 lens.

Examination of cell morphology and sunburn.

Observation of the morphology was performed on paraffin sections after staining with Goldner's variant of Masson's trichrome.

Numbering of sunburn cells (SBC), FIG. 1

Sunburn cells (SBC) were counted throughout each epidermis. The length of each epidermis was measured using the measurement module of the Leica IM1000 and the number of SBC per cm of skin was then calculated.

Number of SBC per cm

|  | Unirradiated | | Irradiated | |
|---|---|---|---|---|
|  | Mean | Standard deviation | Average | Standard deviation |
| Untreated control | 0.6 | 0.4 | 163.8 | 20.5 |
| P1 (urucum extract) | 1.0 | 0.1 | 59.7 | 14.5 |
| P2 (bixin) | 0.3 | 0.4 | 41.9 | 6.1 |
| P3 (norbixin) | 0.3 | 0.4 | 25.5 | 8.7 |

No SBC were observed at day 0. After 7 days of treatment and exposure to ultraviolet radiation, products P1, P2 and P3, respectively, induce a significant reduction (by 63.9%, 74.4% and 84.4%, respectively) of the number of SBC in the epidermis compared to the untreated and irradiated skin.

REFERENCES

Programa conjunto FAO/OMS sobre normas alimentarias. Comision del codex alimentarius 29° periodo de sesiones Ginebra, suiza, 3-7 de julio de 2006.

Informe de la septima reunion del comité del codex sobre la leche y los productos lacteos queenstown, Nueva Zelandia 27 de marzo-1° de abril de 2006. Summary and conclusions of the sixty-seventh meeting of the Joint FAO/WHO Expert committee on food Additives (JECFA) page 2 of 11 issued July 2006.

FDA Code of Federal Regulations. Title 21, Volume 1 Revised as of Apr. 1, 2002. From the U.S. Government Printing Office via GPO Access [CITE: 21CFR73.30] Sec. 73.30 Annatto extract [Pages 346-347].

Agner A. R., Barbisan L. F., Scolastici C., Salvadori D. M. 2004. Absence of carcinogenic and anticarcinogenic effects of annatto in the rat liver medium-term assay. *Food Chem. Toxicol.* 42, 1687-1693.

Bautista A. R. P. L., Moreira E. L. T., Batista M. S., Miranda M. S., Gomes I. C. S. 2004. Subacute toxicity assessment of annatto in rat. *Food Chem. Toxicol.* 42, 625-629.

Biesalski H. K., Obermueller-Jevic U. C. 2001. UV light, beta-carotene and human skin—beneficial and potentially harmful effects. *Arch. Biochem. Biophys.* 389, 1-6.

Corol D-I., Dorobantu I. I., Toma N., Nitu R. 2003. Diversity of biological functions of carotenoids. *Romanian Biotechnol. Lett.* 8, 1067-1074.

Fernandes A. C. S., Almeida C. A., Albano F., Laranja G. A. T., Felzenswalb I., Lage C. L. S., de Sa C. C. N. F., Moura A. S., Kovary K. 2002. Norbixin ingestion did not induce any detectable DNA breakage in liver and kidney but caused a considerable impairment in plasma glucose levels of rats and mice. *J. Nutr. Biochem.* 13, 411-420.

Garmyn M., Ribaya-Mercado J. D., Russell R. M., Bhawan J., Gilchrest B. A. 1995. Effect of β-carotene supplementation on human sunburn reaction. *Exp. Dermatol.* 4, 104-111.

Grollier J. F., Cotteret J., Rosenbaum G. 1991. Light-stable screening cosmetic composition containing bixin combined with a lipid-soluble UV filter and its use for protecting the human epidermis against ultra-violet radiation. Patent WO/5,032,382.

Hagiwara A., Imai N., Ichibara T., Sano M., Tamano S., Aoki H., Yasuhara K., Koda T., Nakamura M., Shirai T. 2003. A thirteen-week oral toxicity study of annatto extract (norbixin), a natural food color extracted from the seed coat of annatto (*Bixa orellana* L.), in Sprague-Dawley rats. *Food Chem. Toxicol.* 41, 1157-1164.

Heinrich U., Gartner C., Wiebusch M., Eichler O., Sies H., Tronnier H., Stahl W. 2003. Supplementation with β-carotene or a similar amount of mixed carotenoids protects Humans from UV-induced erythema. *J. Nutr.* 133, 98-101.

Júnior A. C. T. S., Asad L. M. B. O., de Oliveira E. B., Kovary K., Asad N. R., Felzenszwalb I. 2005. Antigenotoxic and antimutagenic potential of an annatto pigment (norbixin) against oxidative stress. *Genet. Mol. Res.* 4, 94-99.

Kiokias S, and Gordon M. H. 2003. Dietary supplementation with a natural carotenoid mixture decreases oxidative stress. *Eur. J. Clin. Nutr.* 57, 1135-1140.

Kläui H., Korner, W. F. 1973. Light-screening composition and method. U.S. Pat. No. 3,920,834.

Kovary K., Louvain T. S., Costa e Silva M. C., Albano F., Pires B. B. M., Laranja G. A. T., Lage C. L. S., Felzenszwalb I. 2001. Biochemical behaviour of norbixin during in vitro DNA damage induced by reactive oxygen species. *Br. J. Nutr.* 85, 431-440.

Levy L. W., Regalado E., Navarrete S., Watkins R H. 1997. Bixin and norbixin in human plasma: determination and study of the absorption of a single dose of Annatto food color. *Analyst* 122, 977-980.

Levy P. E., Levy L. W. 2003. Supplements containing annatto extracts and carotenoids and methods for using the same. Patent WO03/047528 A2.

Mercadante A. Z., Steck A., Pfander H. 1997. Isolation and structure elucidation of minor carotenoids from annatto (*Bixa orellana* L.) seeds. *Phytochemistry* 46, 1379-1383.

Richelle M., Sabatier M., Steiling H., Williamson G. 2006 Skin bioavailability of dietary vitamin E, carotenoids, polyphenols, vitamin C, zinc and selenium. *Br. J. Nutr.*, 96, 227-238.

Russell K. R. M., Morrison E. Y. St. A., Ragoobirsingh D. 2005. The effect of annatto on insulin binding properties in the dog. *Phytother. Res.* 19, 433-436.

Sies H., Stahl W. 1995. Vitamins E and C, O carotene and other carotenoids as antioxidants. *Am. J. Clin. Nutr.*, 62, 1315S-1321S.

Sies H., Stahl W. 2004. Carotenoids and UV protection. *Photochem. Photobiol. Sci.*, 3, 749-752.

Silva C. R., Antunes L. M. G., Bianchi M. D. L. P. 2001. Antioxidant action of bixin against cisplatin-induced chromosome aberrations and lipid peroxidation in rats. *Pharmacol. Res.* 43, 561-566.

Stahl W., Heinrich U., Jungmann H., von Laar J., Schietel M., Sies H., Tronnier H. 1998. Increased dermal carotenoid levels assessed by noninvasive reflection spectrophotometry correlate with serum levels in women ingesting betatene. *J. Nutr.* 128, 903-907.

Stahl W., Heinrich U., Jungmann H., Sies H., Tronnier H. 2000. Carotenoids and carotenoids plus vitamin E protect against ultraviolet light-induced erythema in humans. *Am. J. Clin. Nutr.* 71, 795-798.

Stahl W., Heinrich U., Wiseman S., Eichler O., Sies H., Tronnier H. 2001. Dietary tomato paste protects against ultraviolet light-induced erythema in humans. *J. Nutr.* 131, 1449-1451.

Stahl W., Heinrich U., Aust. O., Tronnier H., Sies H. 2006. Lycopene-rich products and dietary photoprotection. *Photochem. Photobiol. Sci.* 5, 238-242.

Stahl W., Sies H. 2007. Carotenoids and flavonoids contribute to nutritional protection against skin damage from sunlight. *Mol. Biotechnol.* 37, 26-30.

Thresiamma K. C., George J., Kuttan R. 1998. Protective effect of curcumin, ellagic acid and bixin on radiation induced genotoxicity. *J. Exp. Clin. Cancer Res.*, 4, 431-43.

Trumbo P. R. 2005. Are there adverse effects of lycopene exposure? J. Nutr. 135, 2060S-2061S.

Young A. J., Lowe G. M. 2001. Antioxidant and prooxidant properties of carotenoids. *Arch. Biochem. Biophys.* 385, 20-27.

The invention claimed is:

1. A method of providing an intracellular penetration protection against ultraviolet radiation comprising the step of orally administering a first molecule of formula (I) with R=CH₃ to prevent damage caused by exposure to ultraviolet radiation on mammalian skin at a daily dose between 5 mg and 100 mg

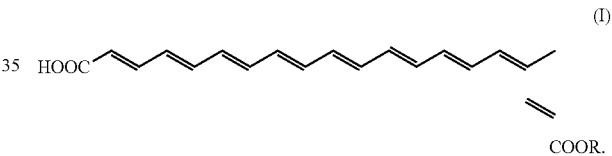

R = H (norbixin) R = CH₃ (bixin)

2. The method according to claim 1, further comprising the step of mixing the first molecule with a second molecule of formula (I) with R=H.

3. The method according to claim 1, further comprising the step of administering the first molecule at a daily dose of 35 mg.

4. The method according to claim 2, further comprising the step of administering the second molecule at a daily dose between 5 mg and 100 mg.

5. A method of providing an intracellular penetration protection against ultraviolet radiation comprising the step of orally administering a first molecule of formula (I) with R=H to prevent damage caused by exposure to ultraviolet radiation on mammalian skin at a daily dose between 5 mg and 100 mg

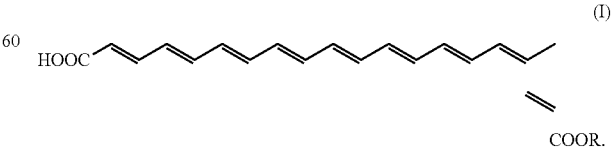

R = H (norbixin) R = CH₃ (bixin)

6. The method according to claim 5, further comprising the step of mixing the first molecule with a second molecule of formula (I) with R=CH$_3$.

7. The method according to claim 5, further comprising the step of enriching an urucum extract in the first molecule of formula (I) with R=H, to prevent damage caused by exposure to ultraviolet radiation on the skin of mammals.

8. The method according to claim 7, further comprising the step of enriching the extract with a second molecule of formula (I) with R=CH$_3$.

9. Medicinal preparation to be orally administered for the intracellular penetration protection of mammalian skin against UV radiation according to claim 5, comprising, in an acceptable carrier to be swallowed, the first molecule of formula (I) with R=H at a minimum rate of 0.001% by weight of the molecule to a maximum dose of 92% by weight of said molecule.

10. The preparation according to claim 9, further comprising a second molecule of formula (I) with R=CH$_3$.

11. The method according to claim 1, further comprising the step of enriching an urucum extract in the first molecule of formula (I) with R=CH$_3$, to prevent damage caused by exposure to ultraviolet radiation on mammalian skin.

12. The method according to claim 11, further comprising the step of enriching the extract with a second molecule of formula (I) with R=H.

13. The method according to claim 11, wherein the extract contains between 2% and 92% by weight of the first molecule.

14. The method according to claim 12, wherein the extract contains between 2% and 92% by weight of the second molecule.

15. Preparation to be orally administered, for the intracellular penetration protection of mammalian skin against UV radiation according to claim 1, comprising, in an acceptable carrier to be swallowed, the first molecule of formula (I) with R=CH$_3$ at a minimum rate of 0.001% by weight of the molecule to a maximum dose of 92% by weight of said molecule.

16. The preparation according to claim 15, further comprising a second molecule of formula (I) with R=H.

17. Preparation according to claim 15, including a minimum dose of 0.001% by weight of the second molecule to a maximum dose of 92% by weight of said second molecule.

18. Preparation according to claim 15, wherein said preparation being a drug.

19. Preparation according to claim 15, wherein said preparation being a dietary supplement or food.

* * * * *